United States Patent
Benz et al.

(10) Patent No.: US 9,179,990 B2
(45) Date of Patent: Nov. 10, 2015

(54) HAND-HELD DENTAL DEVICE

(75) Inventors: Oliver Benz, Gamprin (LI); Dario Tommasini, Mastrils (CH)

(73) Assignee: Ivoclar Vivadent AG, Schaan (LI)

( * ) Notice: Subject to any disclaimer, the term of this patent is extended or adjusted under 35 U.S.C. 154(b) by 245 days.

(21) Appl. No.: 13/328,463

(22) Filed: Dec. 16, 2011

(65) Prior Publication Data
US 2012/0156637 A1 Jun. 21, 2012

(30) Foreign Application Priority Data
Dec. 20, 2010 (EP) .................................... 10196001

(51) Int. Cl.
| A61C 3/03 | (2006.01) |
| A61C 13/15 | (2006.01) |
| H05B 37/00 | (2006.01) |
| A61C 1/00 | (2006.01) |

(52) U.S. Cl.
CPC .............. *A61C 19/004* (2013.01); *H05B 37/00* (2013.01); *A61C 1/0046* (2013.01)

(58) Field of Classification Search
USPC ........................................... 433/29, 118, 119
See application file for complete search history.

(56) References Cited

U.S. PATENT DOCUMENTS

| 5,471,129 A | 11/1995 | Mann et al. |
| 5,634,711 A * | 6/1997 | Kennedy et al. ............... 362/119 |
| 6,095,810 A * | 8/2000 | Bianchetti ........................ 433/29 |
| 6,140,776 A | 10/2000 | Rachwal |
| 6,386,866 B1 * | 5/2002 | Hecht et al. ...................... 433/29 |
| 6,461,568 B1 * | 10/2002 | Eckhardt .......................... 422/24 |
| 6,955,539 B2 * | 10/2005 | Shortt et al. ................... 433/118 |
| 7,104,793 B2 | 9/2006 | Senn et al. |
| 8,568,140 B2 * | 10/2013 | Kovac et al. ..................... 433/29 |
| 2002/0177098 A1 | 11/2002 | Plank |
| 2006/0245187 A1 | 11/2006 | Scott |
| 2007/0273331 A1 | 11/2007 | Cross et al. |
| 2010/0254149 A1 | 10/2010 | Gill |
| 2011/0064977 A1 | 3/2011 | Wendel et al. |
| 2011/0140815 A1 * | 6/2011 | Jamnia ........................... 335/215 |

FOREIGN PATENT DOCUMENTS

| CA | 2304166 A1 | 4/1999 |
| CA | 2383181 A1 | 11/2002 |
| DE | 102004033699 A1 | 2/2006 |
| EP | 1336389 A1 | 8/2003 |
| JP | 2002200100 A | 7/2002 |
| JP | 2002236312 A | 8/2002 |
| JP | 3100119 U | 4/2004 |
| JP | 2004230122 A | 8/2004 |
| JP | 2008061469 A | 3/2008 |
| JP | 2010011668 A | 1/2010 |
| WO | 2010029519 A2 | 3/2010 |

* cited by examiner

*Primary Examiner* — Tung X Le
(74) *Attorney, Agent, or Firm* — Ann M. Knab; Thad McMurray

(57) ABSTRACT

A hand-held light curing apparatus is used with a housing (12), a light source (14), in particular at least one LED, which is connected to a control unit (36), an energy source (20) and at least one energy storage unit in the form of at least one double layer capacitor (26, 28). It is provided that the light source (14) is fed simultaneously by the energy source (20) which is formed as a local energy source such as an accumulator and the double layer capacitor (26, 28).

19 Claims, 2 Drawing Sheets

HAND-HELD DENTAL DEVICE

CROSS-REFERENCE TO RELATED APPLICATIONS

This application claims the benefit of EP Patent Application No. 10196001.1 filed Dec. 20, 2010, which is hereby incorporated by reference in its entirety.

TECHNICAL FIELD

The present invention relates generally to a hand-held dental device.

BACKGROUND

Hand-held dental devices with a light source and an energy source like an accumulator have been known for a long time in dental technology. An example of this is the dental device disclosed in DE 42 11 230 A1 and corresponding U.S. Pat. No. 5,471,129, which is hereby incorporated by reference, in which the light source is powered by rechargeable accumulators.

Cordless light curing devices should not be too heavy, if possible.

Dentists and dental technicians are striving for polymerization cycles to be as short as possible. High-performance LED chips have become available for this in the meantime which allow for light emission cycles of e.g. 20 or 30 seconds.

DE 10 2004 033 699 A1, which is hereby incorporated by reference, discloses a cordless light curing apparatus which is provided with an Ultra-Cap-Capacitor as an energy storage unit. This Ultra-Cap-Capacitor was able to supply the LED chips which were available at that time with enough energy so that 6 or 7 polymerization cycles were possible until the Ultra-Cap-Capacitor had to be recharged.

In the case of too little energy the problem is that the available charge quantity is not sufficient for one polymerization cycle, and this would lead to the fact that non-polymerized monomers would stay in the lower layers of the dental restoration part which is considered very critical as free radicals are suspected to be carcinogenic.

This becomes even more critical as the power of LEDs reaches up to 10 Watts currently, so that even one polymerization cycle might lead to the danger that the charge quantity stored is not sufficient when the local Ultra-Cap-Capacitor has not been charged sufficiently.

A further example of such light curing devices with an Ultra-Cap-Capacitor that have been known for a long time now, is evident from WO 2010/029519, which is hereby incorporated by reference. In this solution, too, the Ultra-Cap-Capacitor that is to replace the batteries known from the prior art, is charged with the aid of a charging device, and is then intended to emit the desired power for the operation of the light source.

Especially with hand-held light-curing devices, in particular pencil-shaped hand-held light-curing devices, the space available for the accommodation of the Ultra-Cap-Capacitor is limited, and the hand-held light-curing device must not be too heavy either.

Attempts have been made to increase the specific power density by using capacitors whose rated voltage is exactly the charge voltage in order to thus realize a capacity as large as possible. In this respect it is disadvantageous, however, that no voltage reserve is available and also that in case of a tolerance of the capacitors, those highly-sophisticated electronic components are overloaded.

In dental practices an explosion of a capacitor would have disastrous consequences, since the materials used in the capacitor are highly toxic and—should the situation arise—would be absorbed by the patient via the mucous membranes thereof.

A further problem of the light curing devices with an Ultra-Cap-Capacitor that have been known for about ten years now, is the necessity to make available a light curing device in the dental practice that is ready to be used any time.

If, for instance, after the light curing of the dental material to be polymerized, which has been applied by the dentist in several layers whereas each layer has been cured at least partially, the dentist discovers that the final curing should take place now, there may not be available enough energy in the Ultra-Cap-Capacitor anymore.

A partial light curing with insufficiently charged capacitors, however, results in the curing of the top layers only, and the lower layers remain uncured for the time being. However, later, in post-curing, these layers contract so that the dental restoration shrinks laterally which leads to the extremely undesired formation of marginal gaps.

Therefore, it is important that enough energy is available for final curing which is typically supposed to take longer than the partial curing of the individual incremental layers of the polymerisation material. Typically, however, the Ultra-Cap-Capacitor has the lowest energy reserves exactly when the demand is highest which can lead to critical situations and rights of recourse towards the dentists.

In order to avoid this it has become established to always make available two light curing devices when using such light curing devices wherein one serves as a reserve in such a situation.

On the other hand, this results in substantial additional costs.

SUMMARY

Rather it is therefore the object of the invention to create a hand-held dental device as set forth in the claims, which are hereby incorporated by reference, which avoids critical situations in dental practices (better) and which makes it possible to manage with only one light curing device for every treatment unit of the dentist.

According to the invention, it is especially favorable that surprisingly the simultaneous energy supply via the accumulator as an energy source on the one hand and via the double layer capacitor on the other hand ensures that it is in a sufficiently charged state even if more than five or six polymerisation cycles are implemented without placing the hand-held dental device into the charging station.

In this connection, the fact that the accumulator or the battery as a local energy source are provided with an especially high specific energy density, at least substantially higher than the Ultra-Cap-Capacitor, can be used especially favorably.

In so far, the advantages of the high power density of the capacitor and the high energy density of the accumulator can be combined especially favorably.

It is provided according to the present invention to combine the local energy source, like for instance a lithium ion accumulator or another accumulator, with at least one additional high-capacity double layer capacitor. The double layer capacitor charged by the energy source is provided with a very high power density of, e.g., 5 W/g and serves as the main energy supplier for the light source.

According to the present invention the voltage which is necessary for the polymerisation is maintained via the local energy source, for instance, by turning on the energy source as the main voltage supplier when the quantity of charge which is stored on the double layer capacitor is exhausted and in this way avoiding that the light output is reduced.

Preferably, the energy source is provided with a relatively high energy density of for instance 100 mWh/g but with a power density which is substantially lower than the power density of the double layer capacitor and which is e.g. 1 W/g.

According to the present invention it is especially favorable that the local energy source simultaneously serves as a safety reserve, even in cases when the capacitor has been discharged by a multiple polymerisation. Then it is possible to undertake controlling in such way that the light curing time is extended automatically in relation to the preset value in order to compensate for the lower light output.

In order to ensure the preferred and favorable distribution of potential, if necessary, a voltage increasing circuit can be used.

It is a matter of course that it is also possible to charge the capacitor while charging the accumulator. The charging voltage of both can be adapted—also in relationship to each other—to the requirements over wide ranges. For instance, the electric double layer capacitor (EDLC) can have a dielectric strength of 2.75 Volt and can be charged to 2.6 Volt while the lithium ion accumulator cells can be charged to 1.25 Volt each, i.e. when using two cells which are connected in series, to 2.5 Volt.

In the present invention it is particularly advantageous when a so-called balancing system is used in most of the capacitors in order to balance voltage and current. This system ensures that all capacitors are provided with the same charge each. This can also be realized when, for instance, two capacitors are connected in parallel and two in series, i.e. when there is an overall arrangement of four capacitors.

The double layer capacitors can have any suitable capacity. Typically, each double layer capacitor is provided with a capacity of at least 1 F but it is also possible to make available an overall capacity of e.g. 200 F with the help of 4 double layer capacitors of 50 F each.

It is particularly favorable that the double layer capacitor which is used as the primary energy storage unit in the present invention is especially suitable to give off a high current. In this way, in pulsed mode a cycle time of less than 10 seconds can be achieved when enough current is applied to the LED chips, and an irradiance of e.g. 10 W/cm$^2$ can be achieved in the present invention without risking an incomplete polymerisation.

In the present invention in this connection it can be made use of the fact that the power density of double layer capacitors is higher than that of lithium ion accumulators by at least one order of magnitude, and depending on the embodiment it is higher by more than two orders of magnitude.

It is particularly favorable in the present invention that with the help of the combination of the high power density when it comes to double layer capacitors and the high energy density when it comes to lithium ion accumulators a high-current pulsed operation is possible without straining the lithium ion accumulator too much as well as a low weight of the handheld dental device in relation to the stored energy.

It is especially favorable when square LED chips, e.g. four chips directly adjacent to each other, are attached to the heat sink for the light source which work at an operating voltage of 3.2 V and are provided with a capacity of 4000 mA due to the connection in parallel. In this embodiment it is favorable when the double layer capacitors are provided with a dielectric strength of 4 V and are charged to 3.6 V by the accumulators of which three are connected in series.

The advantage is that the supply voltage for the LED chips always remains lower than the maximum allowable supply voltage of 3.8 V, and for the EDLC capacitor a safety margin when it comes to its operating voltage exists which is significantly favorable for its life cycle.

When the lithium ion accumulator cells are already discharged half due to the operation in the light curing cycle, they are still provided with an operating voltage of 3×1.15 V, i.e. 3.35 V, so that a safety margin of 3.2 V in relation to the typical operating voltage of LED chips exists, too.

As the overall duration of the treatment is shortened, heat dissipation is simplified, too: While at a duty cycle of e.g. 30 seconds heating takes place over a comparably long period of time in order to ensure a uniformly high temperature level, at a comparably short duty cycle of 10 seconds a temperature peak occurs which can be dissipated easily via a heat buffer. In this way, for instance, the substrate of the LED chips can consist of copper members with a comparably high heat absorption capacity. As secondary heat buffer the double layer capacitors may also be used which—even if only at a low level of temperature—but still basically withstand a heating of up to 20° C. to 50° C. which can be used as heat buffer capacity.

It is favorable when the double layer capacitors are located in the front end of the dental device, in particular close to the light source. The accumulators as local energy sources are then disposed preferably beyond the capacitors so that thermal load is reduced even more.

It is especially favorable in the present invention that the energy source is comprised of at least one energy storage device in the form of at least one double layer capacitor, in particular in addition to the energy source.

It is especially favorable in the present invention that the energy source is formed by at least one in particular chargeable accumulator.

It is especially favorable in the present invention that at least the energy source can be brought into connection with an external energy source via a cable and/or electrical contacts or an inductive interface.

It is especially favorable in the present invention that the device is provided with several, in particular four, double layer capacitors.

It is especially favorable in the present invention that the device is comprised of several, in particular four double layer capacitors which are located in the front end of the dental device, in particular adjacent to the LED.

It is especially favorable in the present invention that the housing consists of several, in particular four, double layer capacitors.

It is especially favorable in the present invention that the double layer capacitors have a capacity of more than one Farad, in particular approximately 4 Farad.

It is especially favorable in the present invention that the double layer capacitors have an energy density of more than 1 Wh/kg, in particular approximately 3 Wh/kg, and a power density of considerably more than 1 W/g, in particular approximately 8 W/g.

It is especially favorable in the present invention that at least 2 of the double layer capacitors are connected in parallel and/or at least 2 of the double layer capacitors are connected in series, which in particular are connected to each other via balancing circuits.

It is especially favorable in the present invention that the double layer capacitor is formed by a lithium ion capacitor.

It is especially favorable in the present invention that the energy source is formed by at least one double layer capacitor and at least one accumulator and/or an external charging unit and/or an external energy supply unit.

It is especially favorable in the present invention that the dental device is provided with at least one first operating mode, in which the energy for the LED is provided by the energy source only, and/or at least one further operating mode in which the energy for the LED is provided by the energy source and in particular by the double layer capacitors, the accumulator or the external electricity supply.

It is especially favorable in the present invention that the light source is provided with at least two LED chips which emit light at wave lengths which are equal to or different from one another, in particular 7 LED chips, of which 6 LED chips emit light not at a wave length of 460 nm to 500 nm, in particular 470 nm, and one LED chip not at a wave length of 380 to 430 nm, in particular 410 nm.

It is especially favorable in the present invention that in at least one exposure mode light is emitted at an irradiance of 500 mW/cm$^2$ to 20,000 mW/cm$^2$, in particular 8,000 mW/cm$^2$ to 12,000 mW/cm$^2$ for a period of two seconds at most, in particular approximately 0.5 seconds to 1.5 seconds.

It is especially favorable in the present invention that the operating modes of the dental device are selectable via an operating unit which is connected to the control device and which outputs acoustical or optical signals.

It is especially favorable in the present invention that the dental device is provided with a heat sink which is thermally connected to the LED for dissipating the heat which is produced by the light source, which heat sink is located in particular at the front end of the housing adjacent to the light source.

It is especially favorable in the present invention that the dental device is formed by a light curing apparatus or by a soft tissue laser.

It is especially favorable in the present invention that the light curing apparatus is provided with a particularly removable light conductor which is located in front of the light source.

BRIEF DESCRIPTION OF THE DRAWINGS

Further advantages, details and features emerge from the following description of an exemplary embodiment with reference to the drawing, in which.

DETAILED DESCRIPTION

Figure 1:
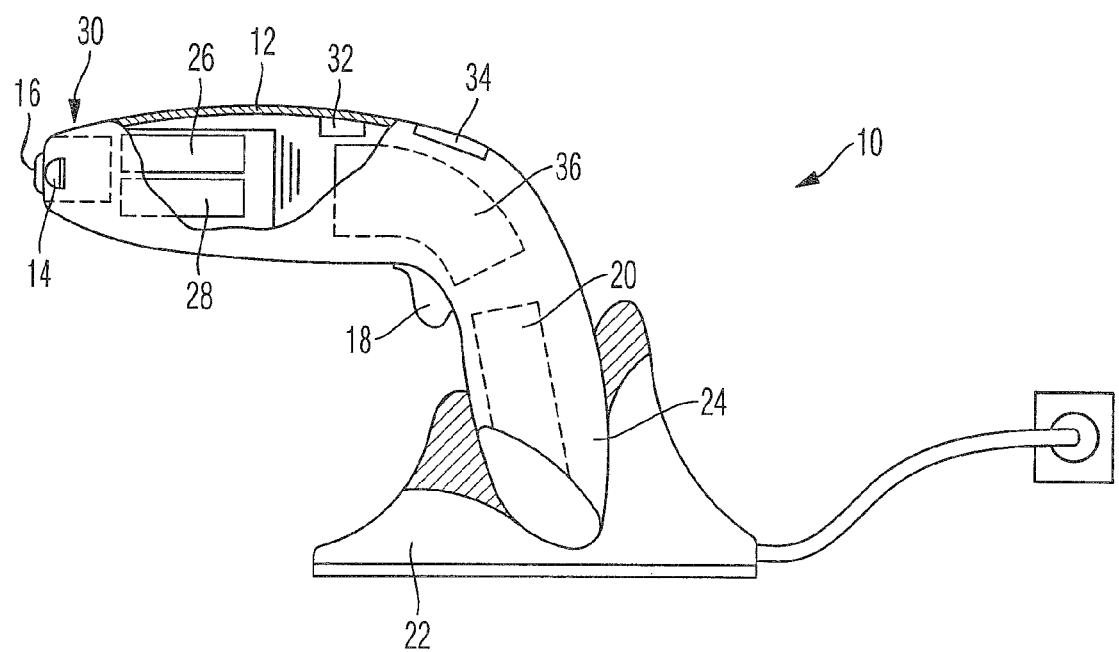
FIG. 1 is a schematic view of a hand-held dental device as an embodiment according to the invention.

The dental device 10 illustrated in FIG. 1 is provided with a substantially pistol-shaped housing 12 in a way known per se. The housing 12 is provided with a light source 14 at its front end in the form of a LED whose emitted light is led to a light conductor in a bundled way.

Furthermore, the housing 12 is provided with a switch 18 with the help of which the dental device 10 can be turned on for the emission of light. In the hand grip 24 of the housing 12 an accumulator 20 is provided as an energy source 20 in a way known which accumulator consists preferably of a plurality of individual accumulator cells. In order to recharge the accumulator 20 a charging unit 22 is provided which is provided with a recess into which the hand grip 24 of the housing 12 fits. When adjusting the hand grip 24 to the recess of the charging unit 22 electrical contacts are made at the same time which ensure the voltage supply of the dental device 10 which is formed as a hand-held device.

In the present invention a plurality of double layer capacitors 26, 28 are located in the housing 12 wherein FIG. 1 illustrates two double layer capacitors 26, 28. The capacitors 26, 28 are also located at the front end of the housing 12, however, well behind the light source 14. In order to be cooled down the light source 14 is mounted on a heat sink 30 which extends directly behind the light source 14. If necessary, the capacitors 26, 28 can have a thermal conductive connection to the heat sink 30 in order to allow for an even higher heat capacity without affecting the capacitors 26, 28 too much by the heat emission. Above and below the heat sink 30 layers of cooling air are provided which make possible convection cooling via cooling fins of the heat sink 30.

In the illustrated embodiment the heat capacity of the double layer capacitors 26, 28 is at least double the amount, particularly four times the amount of the heat capacity of the heat sink 30.

In a way known per se the housing 12 receives control elements at its top. This includes an output for instance in the form of a loudspeaker 32 and an operating unit 34. This can include an LCD output unit or a touch screen for adjusting and selecting the polymerisation cycle.

In order to control the dental device 10 a control device 36 is provided which makes it possible to control and monitor all functions.

Even if not illustrated in FIG. 1, it is a matter of course that the heat sink 30 can be provided with cooling fins in a way known per se and that it can also be cooled in a suitable way via a blower which is not illustrated either.

Figure 2:
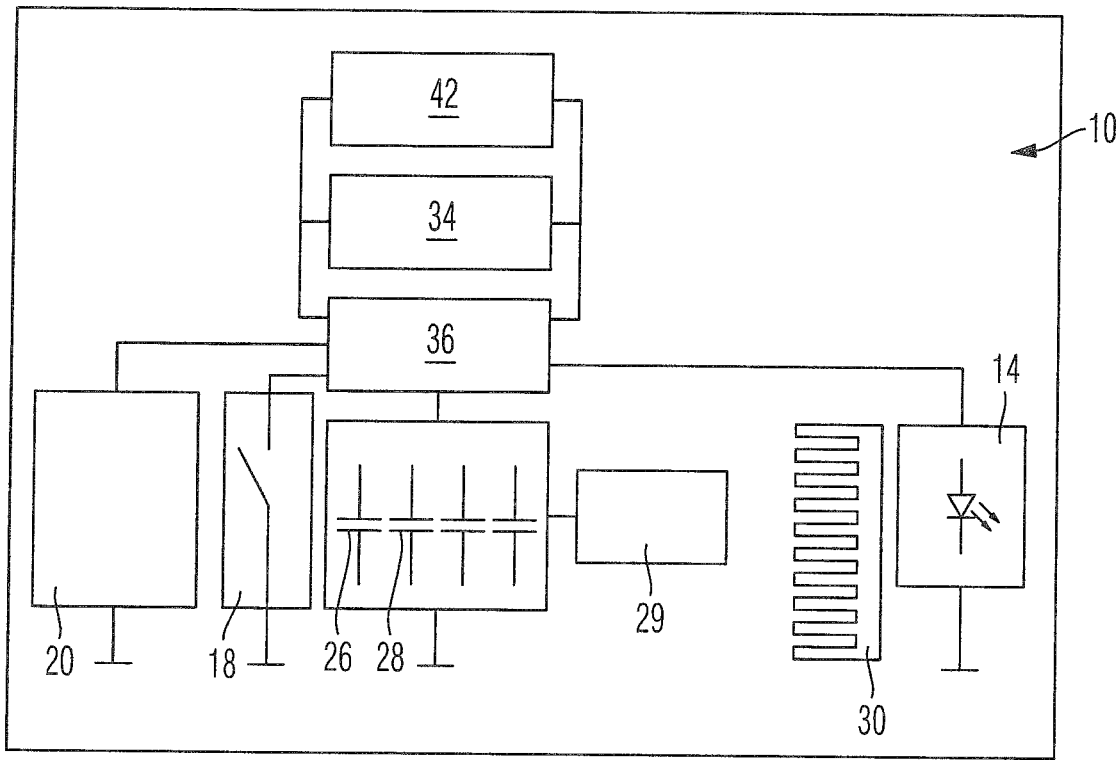
FIG. 2 is a schematic view of a circuit for the dental device as an embodiment according to FIG. 1.

FIG. 2 shows a schematic circuit arrangement for the dental device 10. The circuit arrangement shows the light source 14 which consists of a multiple array of LED chips and which is located on the heat sink 30, for instance on a joint heat sink 30 for several LED chips.

The multiple array of double layer capacitors 26, 28 is located preferably close to this while here, to simplify matters, four double layer capacitors are shown. In fact, the double layer capacitors 26, 28 are connected with each other via a balancing circuit.

The illustration according to FIG. 2 only shows the emission of light, however, it does not show the charging of the double layer capacitors 26, 28 which can take place via the accumulators 20 on the one hand and via the charging unit 22 on the other hand.

According to the embodiment in FIG. 2 a block diagram is provided which shows the main elements of the light curing device 10 in the present invention. The local energy source 20 is illustrated in the form of a block diagram and is, for instance, provided with an accumulator. The energy source is connected to a control device 36 which as central unit controls the discharge of the accumulator 20 on the one hand and of the double layer capacitors 26, 28 on the other hand in order to supply the light source 14 which is also connected to the control device 36 with energy. For this the control device 36 is provided with a switching element which is not shown in the illustration and which ensures switching in the desired way.

The polymerisation cycle is triggered via a switch 18 which is also connected to the control device 36 and which activates a programmable timer which conducts charge from the double layer capacitors 26, 28 and simultaneously from the accumulator 20 to the light source 14 for a predetermined period of time. When the charge in the double layer capacitors 26, 28 is not sufficient anymore, i.e. when voltage has become too low at this point, in a favorable embodiment of the present invention the exclusive supply of the energy source via accumulators is automatically provided so that the accumulator 20 continues the polymerisation cycle without delay. In this state, the capacitors 26, 28 can take part in the discharge or light curing cycle current-free as their terminal voltage then corresponds to the accumulator voltage.

The double layer capacitors 26, 28, of which four are shown in the embodiment according to FIG. 2, are connected to each other via a balancing circuit 29. This circuit serves to ensure a uniformity of charge on all of the four double layer capacitors.

The control device 36 is also connected to an operating unit 34 which e.g. allows for the setting of the programmable polymerisation time or, for instance, the selection of the calibration mode.

Furthermore, an output unit 42 can be used which can show the desired operating mode and any other parameter of the polymerisation cycle on the one hand and of the dental device 10 on the other hand.

According to the present invention it is also favorable when at least two thirds of the supply current of the light source are provided by the capacitors 26, 28, and at most one third by the accumulators 20, and in this way the high power density of the capacitors can be used in an optimum way. It is to be understood that it is also possible to considerably increase the supply current relationship, e.g. from 2:1 to 5:1 or to even higher values, in adaption to the selected relative dimensioning of the accumulators and the capacitors. In the embodiment shown, the accumulators are provided with approximately the same volume of space as the capacitors whereas it is to be understood that the volume-of-space relationship can also be, for instance, 1:2 or 2:1.

The control unit 36 ensures that the accumulators are charged to their rated voltage when charging the hand-held dental device, i.e. for instance to 3.75 V, and that the double layer capacitors are charged to their operating voltage. This operating voltage can also be 3.5 V or a lower value of e.g. 3.3 V.

In light curing, i.e. during the period of the turning on of the light source, the double layer capacitors 26, 28 are now discharged simultaneously with the accumulators 20. As soon as the light curing device is turned off temporarily, the capacitors 26, 28 are charged by the accumulators at least partially so that their high power density is made available again. This is of course at the expense of the accumulator terminal voltage which is then reduced to, for instance, 3.6 V.

This especially favorable recharging according to the invention also takes place in several exposure times which are executed intermittently within one light curing cycle, even without placing the light curing device into the charging station.

The recharging can be realized even more efficiently by operating the capacitors per se at a lower operating voltage, e.g. at 3.4 V, to which they are charged by the charging station. When the capacitors 26, 28 give off charge when they are in use, e.g. to 3.2 V, a larger voltage difference between the terminal voltage of the accumulators and the terminal voltage of the capacitors is made available then which can be used favorably and which makes possible a harmonization of the emission of light—when considered over several duty cycles of the dental device.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. A hand-held dental light curing device comprising
a housing,
an energy source,
at least one energy storage unit, and
a light source,
each of the energy source and the energy storage unit being selectively connected to the light source via a control device to ensure a continuous voltage supply to the light source, and
the at least one energy storage unit comprising at least one double layer capacitor,
wherein the energy source is located in the housing of the dental device and the light source is selectively fed by the energy source, the double layer capacitor, or both, by the control device.

2. The hand-held dental device as claimed in claim 1 wherein the light source comprises at least one LED.

3. The hand-held dental device as claimed in claim 1, wherein the energy source is formed by at least one chargeable accumulator.

4. The hand-held dental device as claimed in claim 1, wherein at least the energy source is configured to be brought into connection with an external energy source by one or more of a cable, electrical contacts and an inductive interface.

5. The hand-held dental device as claimed in claim 1, wherein a supply current of the light source from the double layer capacitor during an exposure operation has at least twice the value of the supply current from the energy source.

6. The dental device as claimed in claim 1, wherein when the light source is switched off, the double layer capacitor is charged by the energy source to adopt the rated voltage thereof.

7. The dental device as claimed in claim 1, wherein a monitoring circuit is provided for the charge and/or the voltage of the double layer capacitor by which an exposure operation is configured to only be activated if the voltage and/or the charge are above a given threshold value.

8. The dental device as claimed in claim 1, wherein a monitoring circuit is provided for the charge and/or the voltage of the double layer capacitor by which an exposure operation is configured to then be activated if the double layer capacitor has not yet been completely charged and the charge is above a preset value.

9. The dental device as claimed in claim 1, wherein the dental device during the exposure operation is switched on for a preset time period which is less than 3 seconds.

10. The dental device as claimed in claim 9, wherein the preset time period is approximately 1 second.

11. The dental device as claimed in claim 1, wherein the light source emits light with an irradiance of 4,000 to 20,000 $mW/cm^2$.

12. The dental device as claimed in claim 1, wherein the LED comprises at least one LED chip which is mounted on a heat sink, wherein the heat sink comprises cooling fins that are configured to be cooled with the aid of a cooling air stream which is generated by a fan.

13. The dental device as claimed in claim 1 wherein a separate cooling device is provided that interacts with the double layer capacitor.

14. The dental device as claimed in claim 13 wherein the separate cooling device provides convection cooling for the double layer capacitor.

15. The dental device as claimed in claim 1, wherein the cooling air stream between the light source and the double layer capacitor substantially extends perpendicular to the light exit direction through the dental device and also cools the power supply lines of the light source.

16. The dental device as claimed in claim 1, wherein the double layer capacitor comprises several individual capacitors that are connected in parallel and/or in serial, and in combination with a voltage and current homogenization circuit, form a balancing system.

17. The dental device as claimed in claim 1, wherein the double layer capacitor comprises at least one lithium ion capacitor.

18. A method of using the dental device as claimed in claim 1, comprising curing of light-polymerizable dental material, wherein the light-polymerizable dental material is present in incremental layer thicknesses of at least 4 mm, and wherein the curing occurs in less than 3 seconds.

19. A method of using the dental device as claimed in claim 1, comprising curing of light-polymerizable dental material that comprises a germanium initiator and/or at least one other photo initiator.

* * * * *